(12) United States Patent
Iwade et al.

(10) Patent No.: US 9,689,654 B2
(45) Date of Patent: Jun. 27, 2017

(54) SELECTION ASSISTING METHOD AND SELECTION ASSISTING APPARATUS

(71) Applicant: Bridgestone Sports Co., Ltd., Tokyo (JP)

(72) Inventors: Hirotada Iwade, Chichibu (JP); Tatsuya Ishikawa, Chichibu (JP); Shintaro Yoshida, Minato-ku (JP)

(73) Assignee: Bridgestone Sports Co., Ltd., Tokyo (JP)

( * ) Notice: Subject to any disclaimer, the term of this patent is extended or adjusted under 35 U.S.C. 154(b) by 0 days.

(21) Appl. No.: 15/141,266

(22) Filed: Apr. 28, 2016

(65) Prior Publication Data

US 2016/0339313 A1  Nov. 24, 2016

(30) Foreign Application Priority Data

May 21, 2015  (JP) ................. 2015-103996

(51) Int. Cl.
| | |
|---|---|
| *A63B 53/14* | (2015.01) |
| *A63B 49/08* | (2015.01) |
| *G01B 5/00* | (2006.01) |
| *G06F 3/00* | (2006.01) |
| *G06F 19/00* | (2011.01) |
| *G06F 1/32* | (2006.01) |
| *G06F 3/01* | (2006.01) |
| *G09B 19/00* | (2006.01) |
| *G06Q 10/06* | (2012.01) |
| *A61B 5/107* | (2006.01) |
| *A61B 5/00* | (2006.01) |

(52) U.S. Cl.
CPC .......... *G01B 5/0023* (2013.01); *G06F 1/3206* (2013.01); *G06F 3/00* (2013.01); *G06F 3/014* (2013.01); *G06F 19/00* (2013.01); *G09B 19/0038* (2013.01); *A61B 5/1072* (2013.01); *A61B 5/6825* (2013.01); *G06Q 10/0639* (2013.01)

(58) Field of Classification Search
USPC ....... 473/131, 239, 282, 407, 409, 223, 299, 473/300
See application file for complete search history.

(56) References Cited

U.S. PATENT DOCUMENTS 4,272,077 A * 6/1981 Spivey .................. A63B 53/14
                                                      473/300
8,057,327 B2   11/2011 Todd
(Continued)

FOREIGN PATENT DOCUMENTS

| JP | 2001-511045 A | 8/2001 |
| JP | 2002-119621 A | 4/2002 |
| WO | 98/34684 A1 | 8/1998 |

*Primary Examiner* — Nini Legesse
(74) *Attorney, Agent, or Firm* — Sughrue Mion, PLLC (57) ABSTRACT

The present invention relates to a selection assisting method including a first selection step of selecting a recommended grip from a plurality of types of grips based on information on a hand size of a testing golfer; a measurement step of measuring by using a measurement device a swing characteristic of the testing golfer in a shot by using a golf club to which the recommended grip selected in the first selection step is attached; and a second selection step of selecting a recommended grip from the plurality of types of grips based on a measurement result in the measurement step.

6 Claims, 7 Drawing Sheets

(56) References Cited

U.S. PATENT DOCUMENTS

| | | | | |
|---|---|---|---|---|
| 8,579,731 | B2* | 11/2013 | Gadiyar | G06Q 30/0641 |
| | | | | 33/262 |
| 8,926,454 | B2* | 1/2015 | Solheim | G06T 7/60 |
| | | | | 382/286 |
| 9,403,059 | B1* | 8/2016 | Johannesen | G06Q 30/0621 |
| 2003/0008731 | A1* | 1/2003 | Anderson | A63B 24/0003 |
| | | | | 473/407 |
| 2006/0287118 | A1* | 12/2006 | Wright | A63B 24/0003 |
| | | | | 473/131 |
| 2009/0088276 | A1* | 4/2009 | Solheim | A63B 24/0003 |
| | | | | 473/409 |
| 2009/0131189 | A1* | 5/2009 | Swartz | A63B 24/0003 |
| | | | | 473/221 |
| 2014/0378238 | A1 | 12/2014 | Voges et al. | |

* cited by examiner

| TYPE | FEATURE | DIAMETER (mm) | | | | | | | | | | |
|---|---|---|---|---|---|---|---|---|---|---|---|---|
| | | 0 | 1 | 2 | 3 | 4 | 5 | 6 | 7 | 8 | 9 | 10 |
| G1 | EXTREMELY THIN | 26.3 | 23.4 | 21.8 | 20.6 | 19.9 | 19.2 | 19.0 | 18.7 | 18.6 | 18.0 | 17.9 |
| G2 | THIN | 26.9 | 23.9 | 22.1 | 21.2 | 20.4 | 19.6 | 19.5 | 19.0 | 18.7 | 18.3 | 18.0 |
| G3 | STANDARD | 28.3 | 24.5 | 22.3 | 21.4 | 20.9 | 20.2 | 19.6 | 19.4 | 18.7 | 18.3 | 17.7 |
| G4 | THICK | 28.8 | 25.7 | 23.4 | 22.5 | 21.7 | 21.2 | 21.0 | 20.7 | 20.5 | 19.8 | 19.2 |
| G5 | EXTREMELY THICK | 29.7 | 26.3 | 23.6 | 23.4 | 22.7 | 21.9 | 21.6 | 21.0 | 20.9 | 20.5 | 19.5 |
| G6 | SMALL TAPER | 28.6 | 24.5 | 22.7 | 21.5 | 21.0 | 20.6 | 20.2 | 20.0 | 19.8 | 20.0 | 18.3 |
| G7 | LARGE TAPER | 28.4 | 25.8 | 23.7 | 22.4 | 21.5 | 20.8 | 20.0 | 19.6 | 19.1 | 18.6 | 18.1 |

| GLOVE SIZE | RECOMMENDED GRIP |
|---|---|
| ~20 | G1 |
| 21 | G2 |
| 22~23 | G3 |
| 24~25 | G4 |
| 26~ | G5 |

SELECTION ASSISTING METHOD AND SELECTION ASSISTING APPARATUS

BACKGROUND OF THE INVENTION

Field of the Invention

The present invention relates to a selection assisting technique for a grip of a golf club.

Description of the Related Art

Golfers are more and more increasing the tendency to obtain golf clubs more suitable for themselves. Therefore, methods of recommending components of golf clubs suitable for individual golfers have been proposed (for example, Japanese Patent Laid-Open No. 2002-119621, Japanese Patent Laid-Open No. 2001-511045, U.S. Pat. Nos. 8,579,731, 8,057,327, and 4,272,077, U.S. Patent Publication No. 2014/378238, and U.S. Pat. No. 8,926,454).

Of the components of a golf club, a grip is generally selected based on the size of the hand of a golfer. However, the characteristics of the grip sometimes have influence on a golfer's swing.

SUMMARY OF THE INVENTION

It is an object of the present invention to provide a mechanism capable of recommending a grip suitable for a golfer's swing.

According the present invention, there is provided a selection assisting method comprising: a first selection step of selecting a recommended grip from a plurality of types of grips based on information on a hand size of a testing golfer; a measurement step of measuring by using a measurement device a swing characteristic of the testing golfer in a shot by using a golf club to which the recommended grip selected in the first selection step is attached; and a second selection step of selecting a recommended grip from the plurality of types of grips based on a measurement result in the measurement step.

Further features of the present invention will become apparent from the following description of exemplary embodiments (with reference to the attached drawings).

DESCRIPTION OF THE EMBODIMENTS

<First Embodiment>

A selection assisting method according to an embodiment of the present invention will be explained below. This embodiment includes steps of preparing a plurality of testing clubs, and selecting a recommended grip based on the test shot results of the testing clubs. First, the testing clubs will be explained with reference to FIG. 1A.

Figure 1A:
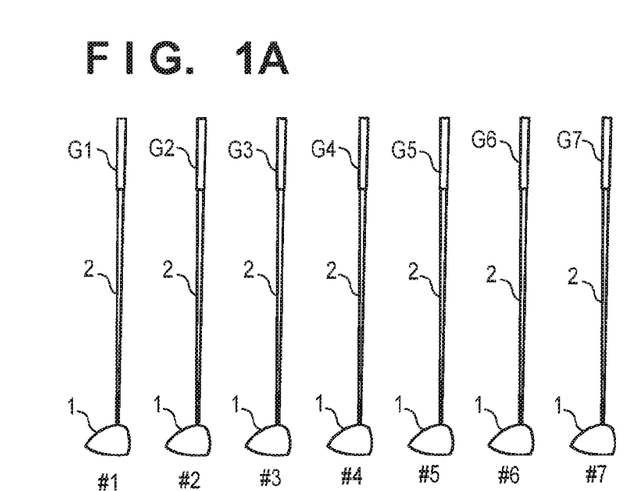
FIG. 1A is a view for explaining testing clubs.

FIG. 1A shows seven testing clubs #1 to #7. Testing clubs #1 to #7 are drivers, but may also be other types of clubs. Testing clubs #1 to #7 are drivers using a common head 1 and common shaft 2, and different in only grip. Grips G1 to G7 are respectively attached to testing clubs #1 to #7.

Figure 1B:
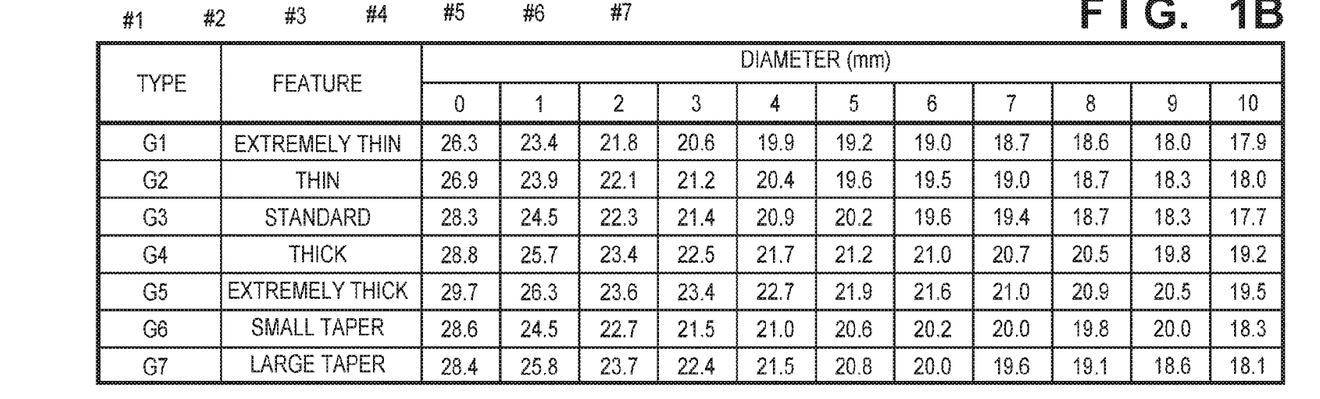
FIG. 1B is a view showing examples of the types of grips.
Figure 1C:
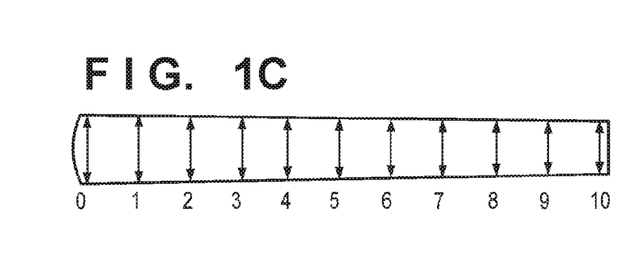
FIG. 1C is a view for explaining the diameters of a plurality of portions of a grip.

In this embodiment, a recommended grip is selected from the seven types of grips G1 to G7. However, the types of grips are not limited to seven types, and may also be eight or more types, or six or less types. FIG. 1B is a view for explaining the specifications of grips G1 to G7, and shows the diameters of the grips in positions 0 to 10 shown in FIG. 1C. Position 0 is the rearmost end, and position 10 is the frontmost end (close to the head 1). The grip diameter is a diameter when the grip is not attached to the shaft.

Grips G1 to G5 are mainly different in grip thickness. Grip G1 is the thinnest grip, and grip G5 is the thickest grip. Grips G6 and G7 are mainly different in shape. This embodiment shows a taper as an example of the grip shape. A taper means the degree of a change in grip diameter from rearmost position 0 to frontmost position 10. A grip having a large difference between the diameters of the rearmost and frontmost ends is called a grip having a strong taper, and a grip having a small difference is called a grip having a weak taper. Grip G6 is a grip having a relatively weak taper, and has a taper weaker than that of grips G1 to G5. Grip G7 is a grip having a relatively strong taper, and has a taper stronger than that of grips G1 to G5. From the viewpoint of thickness, grips G6 and G7 are so designed as to have a thickness close to that of grip G3. Examples of elements characterizing a grip type are the weight, the hardness, and the presence/absence of a backline, in addition to the thickness and shape.

Figure 2:
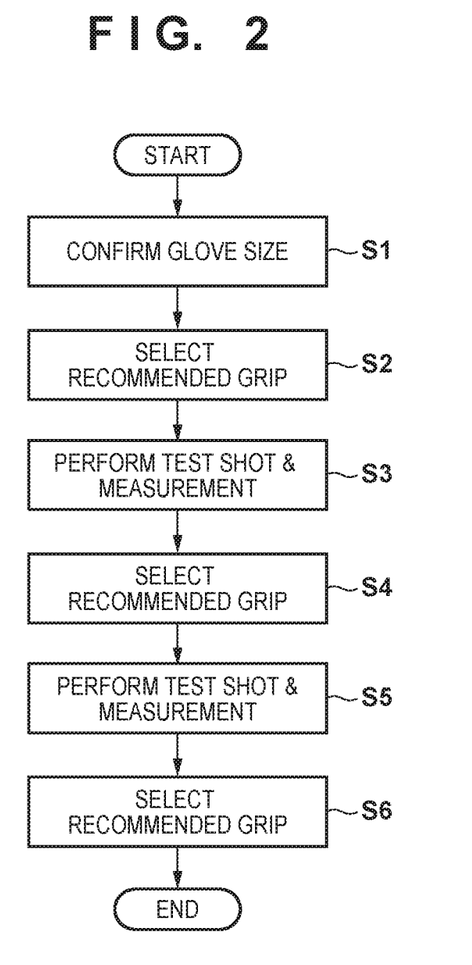
FIG. 2 is a flowchart showing the procedure of a selection assisting method according to an embodiment.
Figure 3A:
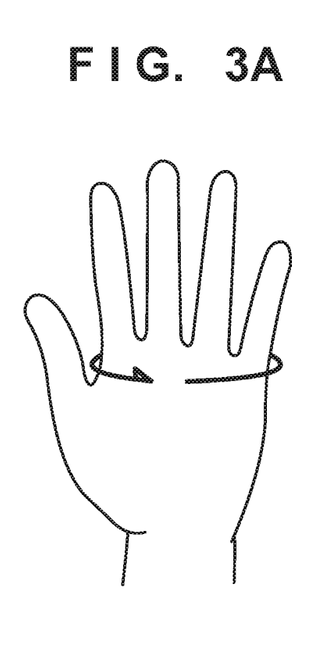
FIG. 3A is a view for explaining an example of measurement of a glove size.

The selection assisting method of this embodiment will be explained with reference to FIG. 2. In step S1, information on the hand size of a testing golfer is confirmed. In this embodiment, the glove size (cm) of the testing golfer is confirmed as this information. The glove size can be confirmed by hearing from the testing golfer. However, if the testing golfer does not know his or her glove size, the glove size can be determined by a method shown in FIG. 3A. That is, as indicated by an arrow in FIG. 1A, the length of the circumference of the palm of a hand is measured in a portion about 1 cm below the root of the little finger, and a value obtained by adding 1 cm to the measured length is used as the glove size.

Figure 3B:
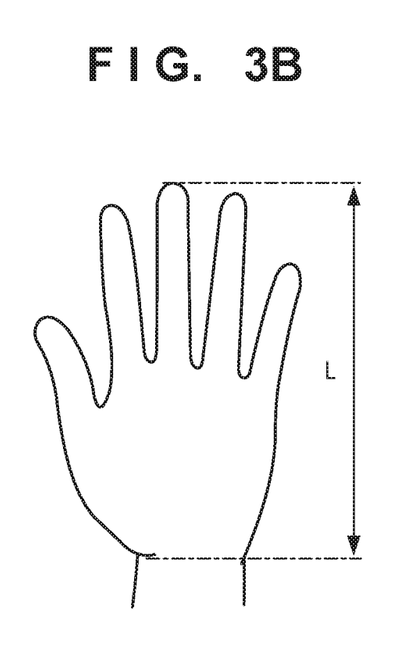
FIG. 3B is a view for explaining an example of measurement of a hand size.

Note that the information on the hand size of the testing golfer may also be a measured value of the hand size of the testing golfer, instead of the glove size. FIG. 3B shows a measurement example. In this example shown in FIG. 3B, a length L from the lowermost end of the palm of a hand to the fingertip is used as the hand size.

Figure 3C:
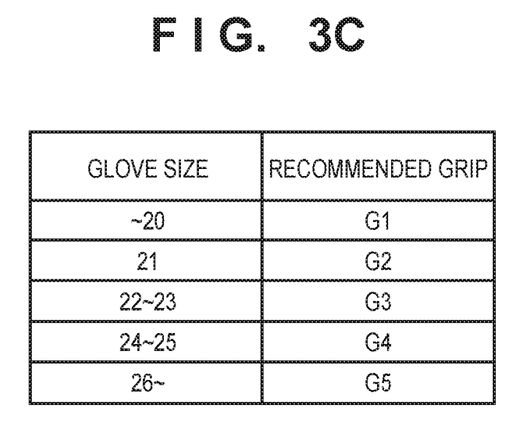
FIG. 3C is a view showing an example of the relationship between the glove size and a recommended grip.

Referring to FIG. 2 again, in step S2, a recommended grip is selected from grips G1 to G5 for the first time based on the information confirmed in step S1. In this embodiment, the relationship between the glove size and a recommended grip is predetermined, and a recommended grip is selected in accordance with this relationship. FIG. 3C shows an example of the relationship between the glove size and a recommended grip in this example shown in FIG. 3C, grip G1 is selected as a recommended grip when the glove size is 20 cm or less. Also, grip G4 is selected as a recommended grip when the glove size is 24 to 25 cm.

The recommended grip selected in step S2 is a grip having a thickness fitting the hand size of the testing golfer. Depending on the swing characteristic of the testing golfer, however, a grip different from this grip may be more suitable for the testing golfer. In step S3, therefore, the testing golfer actually strikes a golf ball by using a golf club to which the recommended grip selected in step S2 is attached, and the swing characteristic of the testing golfer is measured. For example, if the recommended grip selected in step S2 is grip G2, the testing golfer makes a test shot by using golf club #2 shown in FIG. 1A.

Figure 4A:
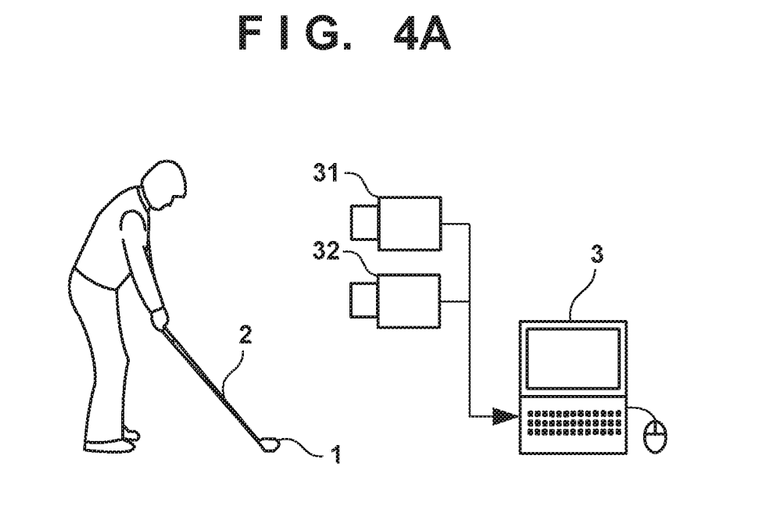
FIGS. 4A and 4B are views for explaining examples of a measurement device.
Figure 4B:
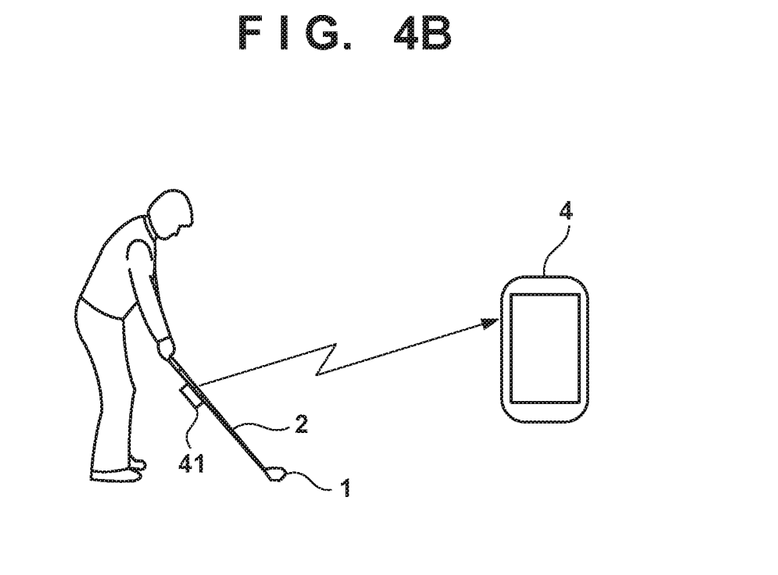

As a measurement device, it is possible to use a device which measures the motion of a golf club being swung (for example, the motion of the head 1), or a device which measures the motion of a struck ball. FIGS. 4A and 4B show examples of the measurement device for measuring the swing characteristic.

The measurement device shown in FIG. 4A includes a personal computer 3 and a plurality of imaging devices 31 and 32. The personal computer 3 has a function of processing images captured by the imaging devices 31 and 32. The imaging devices 31 and 32 are, for example, video cameras, and are so arranged as to have different imaging directions or different imaging ranges. Although this embodiment uses the two imaging devices 31 and 32, but one imaging device need only be used depending on measurement contents. The golfer makes a test shot in a test shot room or the like. In the test shot room or the like, the plurality of imaging devices 31 and 32 capture images of the testing golfer, head 1, and shaft 2, thereby capturing an image of the behavior of the testing club. The personal computer 3 receives the captured image as characteristic data and analyzes the data.

The measurement device shown in FIG. 4B includes a portable terminal 4 and sensor 41. The portable terminal 4 is, for example, a smartphone, and has a near-field wireless communicating function with respect to the sensor 41. The sensor 41 is attached to a golf club, and measures the three-dimensional behavior of the club. For example, the sensor 41 is a nine-axis sensor (three axes for acceleration, three axes for angular velocity, and three axes for directions). The sensor 41 is attached to, for example, the shaft 2. When the testing golfer makes a test shot, the sensor 41 measures the behavior, and transmits a plurality of types of characteristic data as the measurement results to the portable terminal 4. The portable terminal 4 directly uses the received characteristic data, or converts the received data into characteristic data having a predetermined format.

Figure 5A:
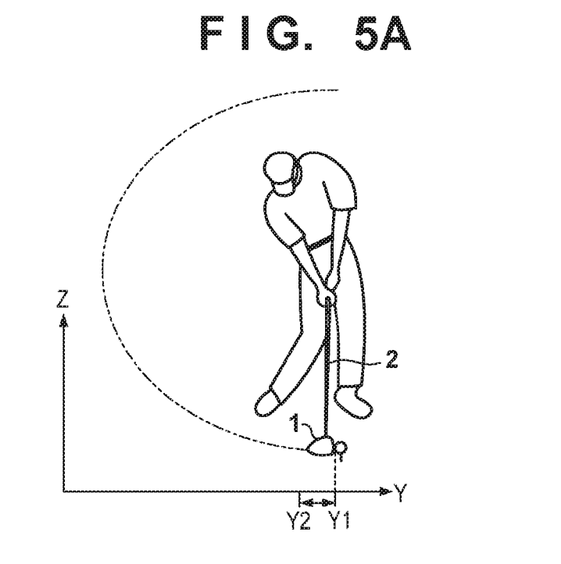
FIG. 5A is a view for explaining the moving range of a head.
Figure 5B:
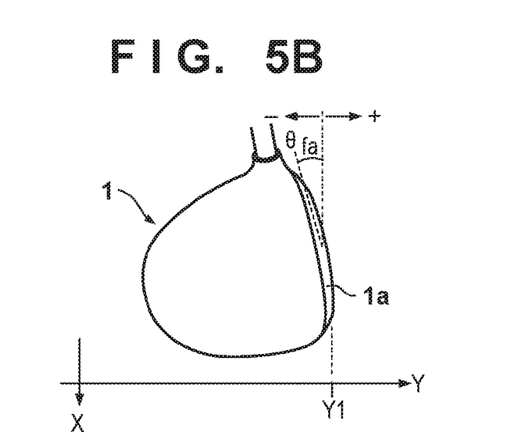
FIG. 5B is a view for explaining an example of a swing characteristic.

In this embodiment, the swing characteristic measured in step S3 is the direction of a face (an impact face angle) at impact. FIGS. 5A and 5B are views for explaining this impact face angle. Assume a virtual three-dimensional space in which a horizontal line parallel to a ball line direction is the Y-axis, a horizontal direction perpendicular to the Y-axis is the X-axis, and a vertical direction is the Z-axis. Note that these coordinate axes may also be set by assuming that the moving direction of the head immediately after takeback is the Y-axis direction. The impact face angle is the direction of a face 1a of the head 1 in an impact position Y1. In this embodiment, the impact face angle is an angle θfa which the X direction and face 1a make on the X-Y plane. The angle θfa can be regarded as 0 at addressing. The angle θfa is a+angle in a direction in which the face 1a opens, and a−angle in a direction in which the face 1a closes.

Figure 5C:
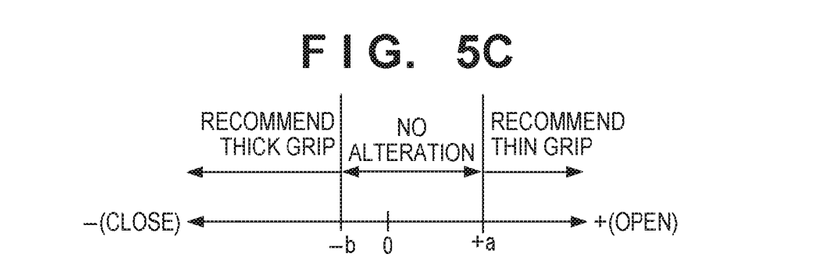
FIG. 5C shows an example of the relationship between the swing characteristic and a recommended grip.

Referring to FIG. 2 again, in step S4, a recommended grip is selected from grips G1 to G5 for the second time based on the measurement result in step S3. In this embodiment, the relationship between the angle θfa and a recommended grip is predetermined, and a recommended grip is selected in accordance with this relationship. FIG. 5C shows an example of the relationship between the angle θfa and a recommended grip. The abscissa is the angle θfa.

If the face 1a opens at impact, a struck ball slices. On the other hand, a golf club having a thin grip facilitates face rotation, so the face 1a readily closes at impact. Accordingly, as the face 1a is more open, a grip to be selected becomes thinner. In the example shown in FIG. 5C, if the angle θfa is +a or more, a grip thinner than the recommended grip selected in step S2 is recommended. For example, if the recommended grip selected in step S2 is grip G4, one of grips G1 to G3 is selected as a recommended grip. In this case, a grip thinner by one grade may also be selected. More specifically, if the recommended grip selected in step S2 is grip G4, grip G3 is selected as a recommended grip. If there is no grip thinner than the recommended grip selected in step S2, the recommended grip selected in step S2 is selected. If the angle θfa is +a or more as described above, slice can be reduced by recommending a thinner grip.

If the face 1a closes at impact, a struck ball hooks. On the other hand, a golf club having a thick grip suppresses face rotation, thereby suppressing closing of the face 1a at impact. Therefore, as the face 1a is more closed, a grip to be selected becomes thicker. In the example shown in FIG. 5C, if the angle θfa is −b or less, a grip thicker than the recommended grip selected in step S2 is recommended. For example, if the recommended grip selected in step S2 is grip G1, one of grips G2 to G5 is selected as a recommended grip. In this case, a grip thicker by one grade may also be selected. More specifically, if the recommended grip selected in step S2 is grip G1, grip G2 is selected as a recommended grip. If there is no grip thicker than the recommended grip selected in step S2, the recommended grip selected in step S2 is selected. If the angle θfa is −b or less as described above, hook can be reduced by recommending a thicker grip.

In the example shown in FIG. 5C, if the angle θfa is larger than −b and smaller than +a, the recommended grip selected in step S2 is selected. When the angle θfa falls within this threshold range, it is conceivable that the face 1a is neither open nor closed largely, so the recommended grip selected in step S2 is suitable.

The threshold values +a and −b shown in FIG. 5C can be determined from test shot experiments conducted by a plurality of testers. The value of +a can be set within the range of, for example, +8 to +12, and can particularly be set at +10. The value of −b can be set within the range of, for example, −7 to −3, and can particularly be set at −5.

The threshold values are two, that is, +a and −b in this embodiment, but they may also be three or more. In this case, as the absolute value of the angle θfa increases, it is possible to increase the change in grade of thickness with respect to the recommended grip selected in step S2. For example, as the angle θfa increases, a grip thinner by two or three grades can be selected as a recommended grip. Likewise, as the angle θfa decreases, a grip thicker by two or three grades can be selected as a recommended grip.

Depending on the swing characteristic of the testing golfer, grip G6 or G7 is sometimes more suitable than grips G1 to G5. In step S5, therefore, the testing golfer practically strikes a golf ball by using a golf club to which the recommended grip selected in step S4 is attached, thereby remeasuring the swing characteristic of the testing golfer. For example, if the recommended club selected in step S4 is grip G3, the testing golfer makes a test shot again by using golf club #3 shown in FIG. 1A.

Figure 6A:
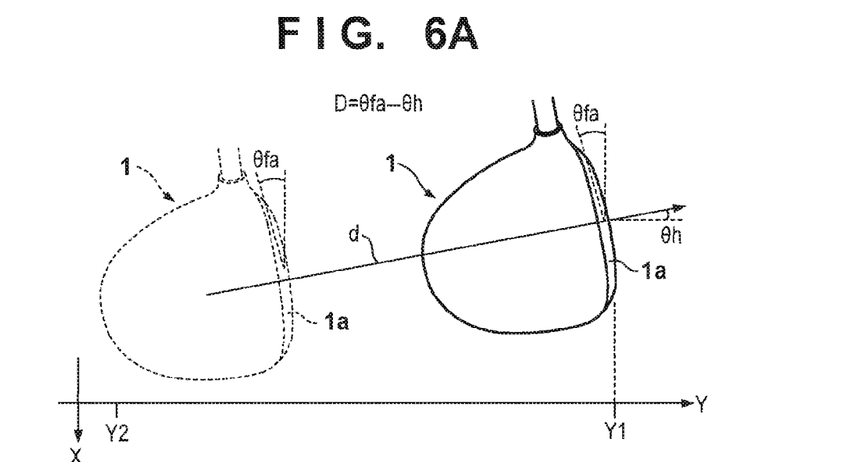
FIGS. 6A and 6B are views for explaining an example of the swing characteristic.

In this embodiment, the swing characteristic measured in step S5 differs from that measured in step S3. In step S5 of this embodiment, the degree of the change in direction of the face (a face change rate) with respect to the moving direction of the head is measured in the moving range (impact zone) of the head from the impact position to a position at a predetermined distance before the impact position. FIGS. 5A and 6A are views for explaining the face change rate.

As shown in FIG. 5A, the impact zone is a zone (for example, 50 cm) from the impact position Y1 to a position Y2 after the ball line. A head orbit in the impact zone is a moving direction d of the head 1 in the impact zone. In this embodiment, the head orbit is an angle θh which the Y direction and the moving direction of the head 1 make. The moving direction of the head 1 can be, e.g., a direction connecting the positions of the head 1 in the impact position Y1 and position Y2. The larger the angle θh, the stronger the tendency of outside-in or inside-out.

Figure 6B:
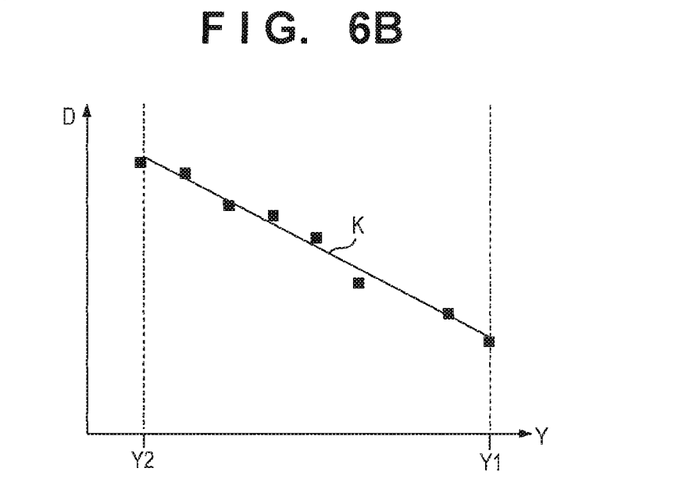

A direction D of the face 1a with respect to the moving direction d of the head 1 is represented by D=θfa−θh. When the direction D is calculated at a plurality of positions in the impact zone and plotted on a coordinate plane in which the position of the head 1 in the Y-axis direction and the direction D are the coordinate axes as shown in FIG. 6B, the slope of an approximate straight line K is the face change rate. When adopting the coordinate axes shown in FIG. 6B, the face change rate takes a minus value, and the degree of the change in direction of the face increases, that is, the face rotation increases, as the absolute value of the face change rate increases.

Figure 6C:
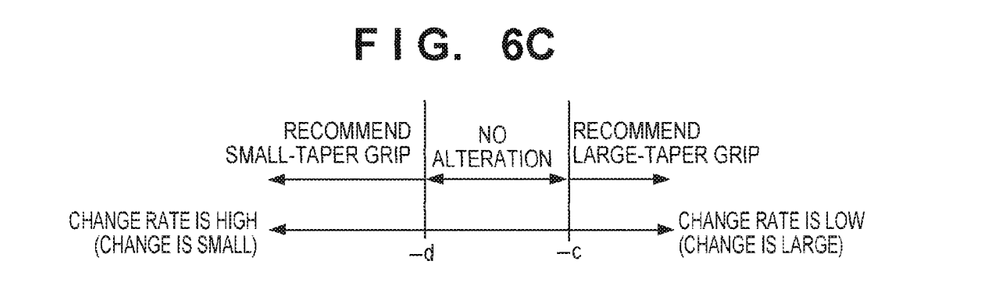
FIG. 6C is a view showing an example of the relationship between the swing characteristic and a recommended grip.

Referring to FIG. 2 again, in step S6, a recommended grip is selected from grips G1 to G7 for the third time, based on the measurement result in step S5. In this embodiment, the relationship between the face change rate and a recommended grip is predetermined, and a recommended grip is selected in accordance with this relationship. FIG. 6C shows an example of the relationship between the face change rate and a recommended grip. The abscissa indicates the face change rate. Since the face change rate takes a minus value as described above, the value of the face change rate decreases (the absolute value increases), that is, the change in face 1a (the face rotation) increases toward the right side on the abscissa shown in FIG. 6C. On the other hand, the value of the face change rate increases (the absolute value decreases), that is, the face rotation decreases toward the left side on the abscissa shown in FIG. 6C.

A golf club which facilitates face rotation is suitable for a testing golfer having a large face rotation. A Golf club to which a grip having a strong taper is attached increases the playability and facilitates face rotation. Accordingly, as the degree of the change in direction of the face increases, a grip having a stronger taper is recommended. In the example shown in FIG. 6C, grip G7 is recommended if the face change rate is −c or less.

A golf club which hardly changes the direction of the face 1a is suitable for a testing golfer having a weak face rotation. A golf club to which a grip having a weak taper is attached decreases the playability and hardly causes face rotation. Therefore, as the degree of the change in direction of the face decreases, a grip having a weaker taper is recommended. In the example shown in FIG. 6C, grip G6 is recommended if the face change rate is −d or more.

In the example shown in FIG. 6C, the recommended grip selected in step S4 is selected if the face change rate is lower than −d and higher than −c. When the face change rate falls within this threshold range, it is conceivable that the face rotation of the testing golfer is average, so the recommended grip selected in step S4 is suited.

The threshold values −c and −d shown in FIG. 6C can be determined from test shot experiments conducted by a plurality of testers. The value of −c can be set within the range of −27 to −33 deg/m, and can particularly be set at −30 deg/m. The value of −d can be set within the range of −18 to −22 deg/m, and can particularly be set at −20 deg/m.

Thus, the grip selected in step S6 is a final recommended grip. This makes it possible to recommend a grip fitting the hand size of a golfer and suited to the swing of the golfer.

<Second Embodiment>

In the first embodiment, a final recommended grip is selected by three stages (steps S2, S4, and S6) based on the glove size (step S1), swing characteristic (step S3), and swing characteristic (step S5). However, a final recommended grip may also be selected by two stages. For example, the recommended grip selected in step S4 may also be selected as a final recommended grip by omitting steps S5 and S6. It is also possible to select a final recommended grip by two stages by omitting, for example, steps S3 and S4. More specifically, it is possible to perform a test shot and measurement as in step S5 by using a golf club to which the recommended grip selected in step S2 is attached, and select, as a final recommended grip, a grip selected by the same method as in step S6.

<Third Embodiment>

In the first embodiment, a recommended grip is selected based on the impact face angle in step S4. However, it is also possible to measure the side-spin amount of a struck ball in step S3, and select a recommended grip based on the side-spin amount of the struck ball in step S4. When selecting a recommended grip based on the side-spin amount, it is possible to select a thinner grip if a sliced side-spin amount is equal to or larger than a first threshold value, and select a thicker grip if a hooked side-spin amount is equal to or larger than a second threshold value. The first and second threshold values can be the same value or different values.

Furthermore, in the first embodiment, a recommended grip is selected based on the face change rate in step S6. However, it is also possible to measure the angular velocity around the shaft 2 in the impact zone in step S5, and select a recommended grip based on the angular velocity around the shaft 2 in step S6. In this case, a grip having a stronger taper can be selected if the angular velocity is equal to or higher than a first threshold value, and a grip having a weaker taper can be selected if the angular velocity is equal to or lower than a second threshold value. The first and second threshold values can be the same value or different values.

<Fourth Embodiment>

In the first embodiment, a recommended grip is selected based on one type of swing characteristic in step S4. However, a recommended grip may also be selected based on a plurality of types of swing characteristics. Similarly, a recommended grip is selected based on one type of swing characteristic in step S6, but a recommended grip may also be selected based on a plurality of types of swing characteristics. Examples of the swing characteristic are the head speed and the head orbit in the impact zone, in addition to the above-described swing characteristics.

<Fifth Embodiment>

Figure 7:
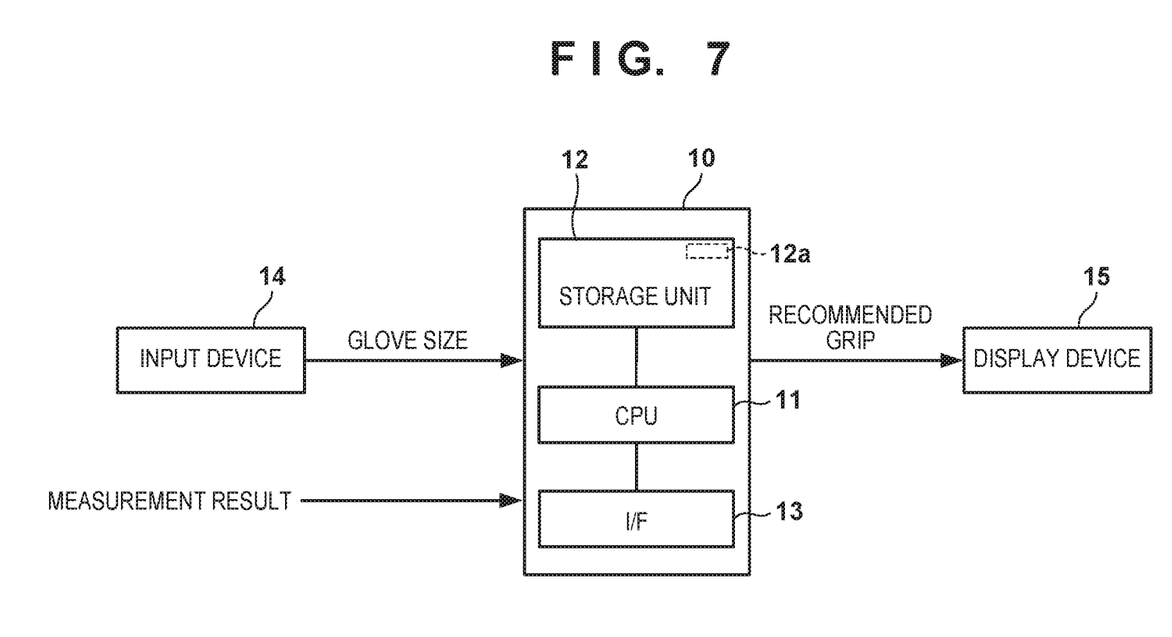
FIG. 7 is a block diagram of a selection assisting apparatus according to an embodiment.

An example of a selection assisting apparatus which performs at least some steps of the above-described selection assisting method will be explained below. FIG. 7 is a block diagram of a selection assisting apparatus 10. The selection assisting apparatus 10 can be configured by using a general personal computer or server computer. The selection assisting apparatus 10 includes a CPU (processor) 11, storage unit 12, and interface 13. The storage unit 12 is, for example, a RAM, ROM, or hard disk. The storage unit 12 stores selection information 12a. The selection information 12a is information for automatically selecting a recommended grip. For example, the selection information 12a contains information indicating the relationship shown in FIG. 3C, information indicating the relationship shown in FIG. 5C, and information indicating the relationship shown in FIG. 6C.

An input device 14, measurement device (not shown), display device 15, and the like are connected to the selection assisting apparatus 10 via the interface 13. The input device 14 includes a keyboard, mouse, and the like, and inputs information on the hand size of a testing golfer, for example, the glove size. The CPU 11 can receive this information, and perform automatic recommended grip selection in step 82 based on the selection information 12a. The CPU 11 can also receive information on the swing characteristic from the measurement device (not shown), and perform automatic recommended grip selection in step S4 or S6 based on the selection information 12a. As the measurement device, the same device as that shown in FIG. 3A or 3B) can be adopted. The display device 15 can display a recommended grip.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-103996, filed May 21, 2015, which is hereby incorporated, by reference herein in its entirety.

What is claimed is:

1. A selection assisting method comprising:
   a first selection step of selecting a recommended grip from a plurality of types of grips based on information on a hand size of a testing golfer;
   a measurement step of measuring by using a measurement device a swing characteristic of the testing golfer in a shot by using a golf club to which the recommended grip selected in the first selection step is attached;
   a second selection step of selecting a recommended grip from the plurality of types of grips based on a measurement result in the measurement step,
   a re-measurement step of measuring by using a measurement device in a shot by using a golf club to which the recommended grip selected in the second selection step is attached; and
   a third selection step of selecting a recommended grip from the plurality of types of grips based on a measurement result in the re-measurement step,
   wherein
   in the measurement step, a direction of a face at impact is measured as the swing characteristic,
   in the re-measurement step, a degree of a change in direction of a face with respect to a moving direction of a head within a moving range of the head from an impact position to a position at a predetermined distance before the impact position is measured as the swing characteristic,
   in the second selection step, the more open the face, the thinner a grip that is selected as the recommended grip, and the more closed the face, the thicker a grip that is selected as the recommended grip, and
   in the third selection step, the larger the degree of the change, the stronger taper of a grip that is selected as the recommended grip, and the smaller the degree of the change, the weaker taper of a grip that is selected as the recommended grip.

2. The method according to claim 1, wherein
   in the second selection step, a grip having a diameter fitting the testing golfer is selected as the recommended grip, and
   in the third selection step, a grip having a tapered shape fitting the testing golfer is selected as the recommended grip.

3. A selection assisting method comprising:
   a first selection step of selecting a recommended grip from a plurality of types of grips based on information on a hand size of a testing golfer;
   a measurement step of measuring by using a measurement device a swing characteristic of the testing golfer in a shot by using a golf club to which the recommended grip selected in the first selection step is attached; and
   a second selection step of selecting a recommended grip from the plurality of types of grips based on a measurement result in the measurement step,
   wherein
   in the measurement step, a direction of a face of a golf club head at impact is measured as the swing characteristic, and
   in the second selection step, the more open the face, the thinner a grip that is selected as the recommended grip, and the more closed the face, the thicker a grip that is selected as the recommended grip.

4. The method according to claim 3, wherein the information is one of a measured value of a glove size of the testing golfer and a measured value of the hand size of the testing golfer.

5. A selection assisting apparatus comprising:
   a first selection unit configured to select a recommended grip from a plurality of types of grips based on information on a hand size of a testing golfer;
   a measurement unit configured to measure a swing characteristic of the testing golfer when the testing golfer strikes a golf ball by using a golf club to which the recommended grip selected by the first selection unit is attached; and
   a second selection unit configured to select a recommended grip from the plurality of types of grips based on a measurement result of the measurement unit,
   wherein the measurement unit measures a direction of a face of a golf club head at impact as the swing characteristic, and
   the second selection unit selects, the more open the face, the thinner a grip as the recommended grip, and the more closed the face, the thicker a grip as the recommended grip.

6. A selection assisting apparatus comprising a processor, a measurement device and a storage unit, the storage unit storing computer readable instructions that, when executed by the processor, cause the apparatus to:

select a recommended grip from a plurality of types of grips based on information on a hand size of a testing golfer;
acquire a measurement result of a swing characteristic of the testing golfer by using the measurement device when the testing golfer strikes a golf ball by using a golf club to which the selected recommended grip is attached; and
select a recommended grip from the plurality of types of grips based on the acquired measurement result,
in the acquiring, a direction of a face of a golf club head at impact is acquired as the swing characteristic, and
in the selecting based on the acquired measurement result, the more open the face, the thinner a grip that is selected as the recommended grip, and the more closed the face, the thicker a grip that is selected as the recommended grip.

* * * * *